United States Patent [19]
Ferek-Petric et al.

[11] Patent Number: 5,840,030
[45] Date of Patent: Nov. 24, 1998

[54] ULTRASONIC MARKED CARDIAC ABLATION CATHETER

[75] Inventors: Bozidar Ferek-Petric; Branko Breyer; Ivo Cikes, all of Zagreb, Croatia

[73] Assignee: Sulzer Osypka GmbH, Grenzach-Wyhlen, Germany

[21] Appl. No.: 666,508

[22] PCT Filed: Dec. 21, 1994

[86] PCT No.: PCT/EP94/04252

§ 371 Date: Jun. 21, 1996

§ 102(e) Date: Jun. 21, 1996

[87] PCT Pub. No.: WO95/17131

PCT Pub. Date: Jun. 29, 1995

[30] Foreign Application Priority Data

Dec. 22, 1993 [HR] Croatia ................................ P 931513A
Dec. 22, 1993 [HR] Croatia ................................ P 931514A

[51] Int. Cl.⁶ ........................................................ A61B 8/00
[52] U.S. Cl. ............................................. 600/439; 607/122
[58] Field of Search ................................ 128/642, 660.03, 128/662.06; 607/9, 122; 600/439

[56] References Cited

U.S. PATENT DOCUMENTS

| | | | |
|---|---|---|---|
| 4,697,595 | 10/1987 | Breyer et al. | 128/660 |
| 4,706,681 | 11/1987 | Breyer et al. | 128/642 |
| 5,295,484 | 3/1994 | Marcus et al. | 128/660.03 |
| 5,385,148 | 1/1995 | Lesh et al. | 128/667.06 |
| 5,409,000 | 4/1995 | Imran | 128/660.03 X |
| 5,454,809 | 10/1995 | Jonssen | 128/660.03 X |

OTHER PUBLICATIONS

Calkins, H. et al., (1991), "Radiation Exposure During Radiofrequency Catheter Ablation of Accessory Atrioventricular Connections," *Circulation* vol. 84, No. 6, pp. 2376–2381.

Langberg, J. et al "The Echo Transponder Electrode Catheter . . . ", JACC vol. 12 No. 1 Jul. 1988/218–223 (copy 128/660.03).

*Primary Examiner*—Francis Jaworski
*Attorney, Agent, or Firm*—Lahive & Cockfield, LLP

[57] ABSTRACT

A method and system for therapy of cardiac arrythmias is provided which uses a directional electric field applied via ablation electrode for cardiac ablation together with an ultrasonic imaging system including an ultrasonic marking transducer mounted fixedly in the vicinity of the ablation electrode and having ultrasonic sensitivity characteristics either in the same direction as the ablation field or in some other direction determined by a certain defined angle relative to the direction of the ablation field.

46 Claims, 9 Drawing Sheets

ULTRASONIC MARKED CARDIAC ABLATION CATHETER

TECHNICAL FIELD

This invention relates to the therapy of cardiac arrhythmias particularly to the system for ablation of the cardiac conduction tissue for the objective of cessation of the cardiac arrhythmia. More particularly, the invention pertains to the system for ablation by means of directional electric field as well as for the orientation of the ablation electrode within the heart. This invention also relates to monitoring of the contact between the ablation electrode and the cardiac tissue.

BACKGROUND AND PRIOR ART

Tachycardia is the condition of the accelerated pulse rate. Natural tachycardia occurs in physical exercise and emotional stress because of the sympathetic nervous tone and increase of the circulatory cathecolamines concentration. The most important quality of the natural tachycardia is the increase of the cardiac output. Pathologic tachycardia is the one which impedes the hemodynamics of the heart i.e. decrease of the cardiac output occurs. The electrophysiology discriminates two major classes of tachycardia: supraventricular and ventricular, as well as two major classes of etiology: ectopic focuses and reentry phenomena. The therapy of tachycardia is in principle either the suppression of ectopic focuses or interruption of the reentry pathway. The first access is always the pharmacotherapy. Despite of the recent advances in electropharmacology, every antiarrhythmic drug is not effective in every patient. Drugs also provoke the side effects which can be hazardous to the patient. Therefore more invasive modes of therapy must be encountered like surgical treatment and permanent implantation of an electrotherapy device. The method of choice is the ablation which is a semi-invasive interventional method.

Transvenous catheter ablation of cardiac conduction tissue is a low risk alternative to surgical ablation to achieve a goal to control refractory supraventricular tachyarrhythmias. Some positive results have been also acquired in the treatment of ventricular tachycardia. The principal energy source for catheter ablations is a DC energy pulse from a standard defibrillator. In order to minimize the energy for the purpose of safety, numerous modifications in design of the energy source as well as of the catheter have been realized. In order to achieve the controllability of the lesion size as well as to avoid hazardous shock wave, the radiofrequency energy source has been introduced. For the same reason, the laser ablation fiberoptic catheters have been developed. The application of microwave energy is an alternative method, as well as the ablation by means of the chemical agents.

One of the problems in ablation is the exact positioning of the ablation electrode within the heart. The procedure is normally controlled by means of the radiographic imaging. Recent investigations proved that X-ray radiation exposure is significant and may be hazardous (H. Calkins et al.: "Radiation Exposure During Radiofrequency Catheter Ablation of Accessory Atrioventricular Connections." Circulation 1991:84:2376 –2382.). Disadvantage of X-ray methods is the poor imaging of soft tissues, i.e. papillary muscle, interventricular septa, and so forth. As an alternative ultrasonic imaging is well suited for imaging of soft tissues, but has the disadvantage of imaging in one plane tomographically. The ultrasonically marked catheters and cardiac pacing leads have been described in the U.S. Pat. No. 4,697,595 and in the U.S. Pat. No. 4,706,681 respectively. Such systems enable the echocardiographic guidance of the procedure as well as the exact localization of the lead tip. If the ablation electrode is marked by an ultrasonic transducer, the exact position of the ablation electrode can be identified. As far as it is known to the inventors none of the systems enables the radial orientation of the catheter.

The majority of ablation catheters comprise ring electrodes producing the axial symmetric field. Therefore dissipation of the ablation energy occurs in the vicinity of the electrode, and only a small portion of the electric field penetrating towards the tissue is efficient. Platelet electrodes mounted on the one side of the catheter body produce directional electric field, but the problem of radial orientation of the catheter occurs. Position of the electrode cannot be monitored by means of the X-ray imaging. It is therefore important to obtain the method of confirmation of directional electric field orientation towards the tissue.

In order to use the maximal amount of ablation electric field, the ablation electrode must have an intimate contact with the cardiac tissue. Because of the cardiac contractions, dislodgement of the electrode from desired position occurs. Electrophysiologists usually monitor the intracardiac potentials to confirm the proper position as well as the proper contact of the electrode with the endocardium. However, the intracardiac potential is discontinuous being characterized with intrinsic deflection which is repetitive at the frequency of the heart beats. Distinct ST elevation caused by the injury current confirms the pressure of the electrode to the cardiac muscle. However, dislodgement may also occur anywhere within the cardiac cycle while there is no intracardiac signal. There is a system available on the market (Made by Dr. Osypka GmbH) which monitors the impedance of the ablation electrode as an indirect parameter for contact monitoring. As far as it is known to the inventors, none of the available systems enables the continuous monitoring of the distance between the electrode and the endocardial cardiac tissue.

SUMMARY OF THE INVENTION

It is a principle object of this invention to provide a system for ablation procedure with the ultrasonically marked catheter comprising means for determination of radial orientation as well as the means for directional field ablation.

It is a particular object of this invention to provide means for determination of the ablation field direction within the heart by means of ultrasonic imaging.

In accordance with a first aspect of the invention, the ablation catheter comprises an ablation electrode producing directional electric field as well as an ultrasonic marking transducer mounted fixedly in the vicinity of the ablation electrode having directional ultrasonic sensitivity characteristics either in the same direction as the ablation field or in some another direction determined by a certain defined angle relatively to the direction of the ablation field.

It is a further object of the invention to provide means for measuring distance of the ablation electrode from the cardiac tissue and means for modulation of the ablation energy source in such a way as to deliver the energy only if the electrode is in the intimate contact with the tissue.

In accordance with further aspect of the invention, an ultrasonic apparatus comprises the electronic circuits capable to measure the distance of the ablation electrode from the tissue as well as to switch on the ablation energy source whenever the electrode is sufficiently close to the tissue. An energy control means may be provided for changing the power of the ablation in response to an output from the proximity measurement means. Further objects, features and advantages of the invention will become apparent upon consideration of the following detailed description in conjunction with the drawings, in which:

DESCRIPTION OF THE PREFERRED EMBODIMENT

Figure 1:
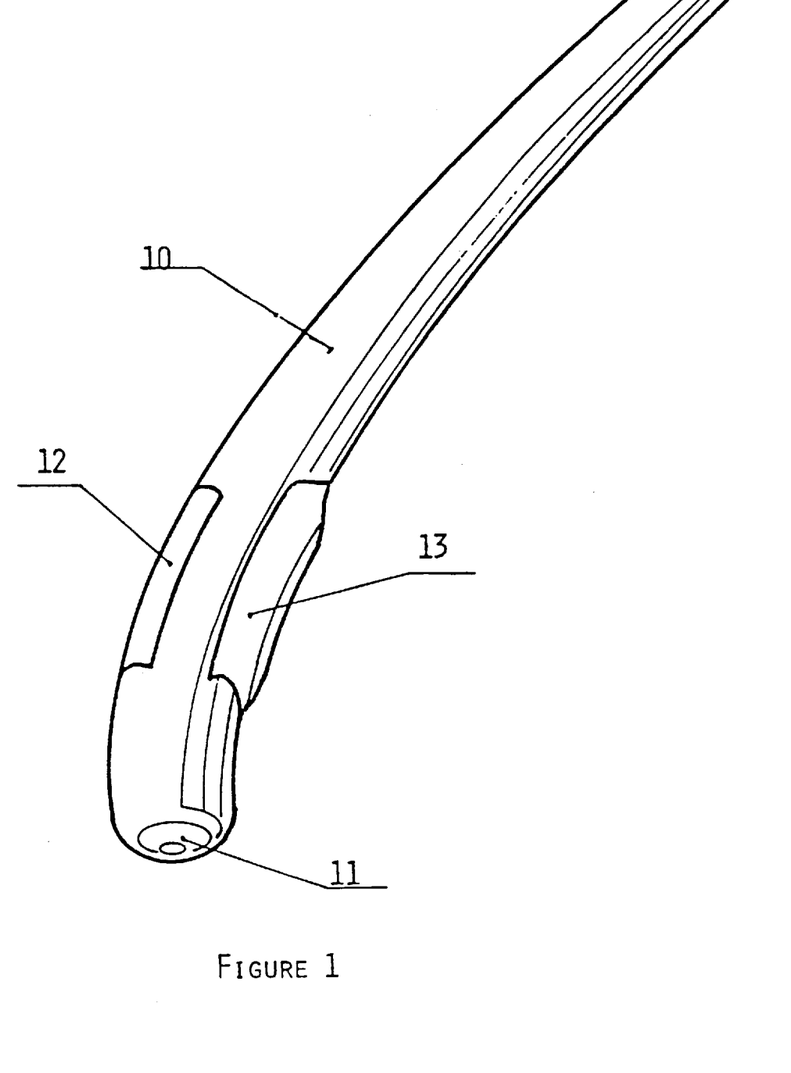
FIG. 1 is a perspective view of an ultrasonically marked ablation catheter providing opposite directions of ultrasonic and electric fields.

Referring to FIG. 1 there is shown a distal part of a catheter comprising a plastic body 10. Adjacent to the catheter tip 11 there is an ablation electrode 12. The ablation electrode 12 is a plate having the maximal width of approximately the quarter of the catheter body circumference. Such an electrode generates directional electric field which penetrates to the side where the electrode is mounted fixedly. It is disclosed that the electrode 12 is embedded within the catheter body 10, but it may be also fixed on the body surface. Disclosed electrode mounting mode is preferable because of the ease of catheter insertion within the blood vessel. At the opposite side to the electrode, an ultrasonic marking transducer assembly 13 is mounted fixed in such a way as to generate the ultrasonic field which is opposite to the electric field for the ablation.

Figure 2:
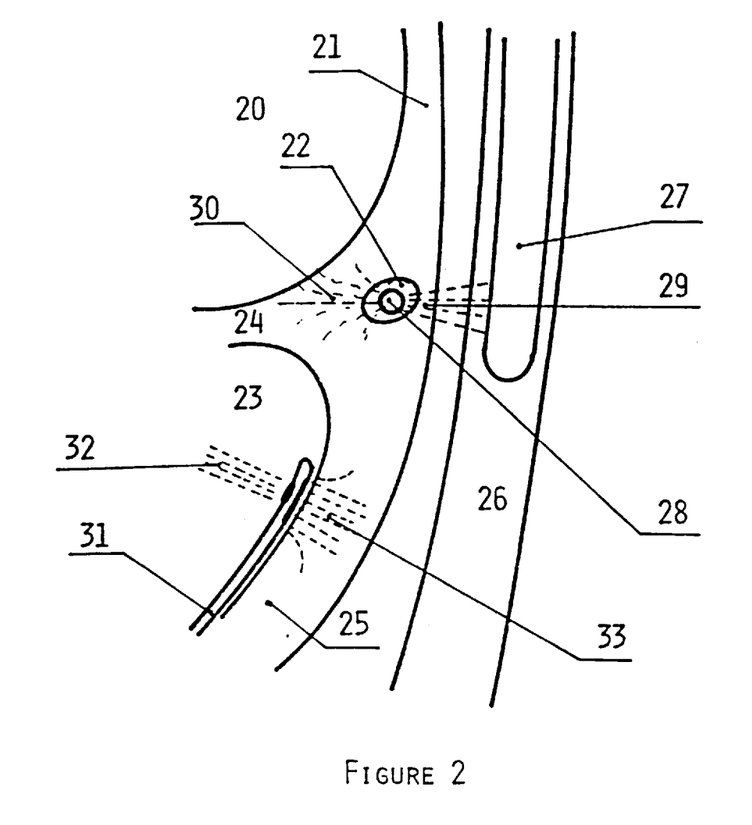
FIG. 2 is a schematic disclosure of application of the catheter from previous figure within the heart.

Referring to FIG. 2 there is disclosed a schematic cross-section through the left posterior heart. The left atrial cavity 20 and the left atrial posterior wall 21 are disclosed as well as the left ventricular cavity 23 and the left posterior ventricular wall 25. Between the atrial cavity 20 and the ventricular cavity 23, there is a fibrous annulus 24 of the mitral valve (not shown), the coronary sinus 22 being posteriorly. The oesophagus 26 is in the intimate contact with the left atrial posterior wall 21. The transoesophageal echocardiography probe 27 is inserted within the oesophagus 26. An ultrasonically marked catheter 28, such as described in previous figure, is implanted within the coronary sinus 22. The catheter 28 generates the ultrasonic field 29 as well as the ablation electric field 30. Disclosed arrangement illustrates the correct position of the ablation catheter such as to obtain the mark on the echocardiographic image by means of the transoesophageal probe 27 and directional ultrasonic field 29. At the opposite side of the catheter, the ablation field 30 is directed towards the fibrous annulus 24 wherein the accessory pathway should be ablated for treatment of supraventricular tachycardia. Radial twisting of the catheter can chance direction of both fields and, by means of the transoesophageal echocardiography imaging, the ablation field can be directed towards preferred cardiac tissue volume. Another ablation catheter 31 is implanted within the left ventricle for the treatment of ventricular tachycardia. Catheter 31 generates an ultrasonic marking field 32 directed anteriorly as well as an ablation electric field 33 directed towards the left ventricular posterior wall 25. By means of the radial twisting of the catheter 31 and two dimensional transthoracic echocardiographic imaging, the ablation field 33 can be directed towards preferred volume of the ventricular wall 25.

Figure 3:
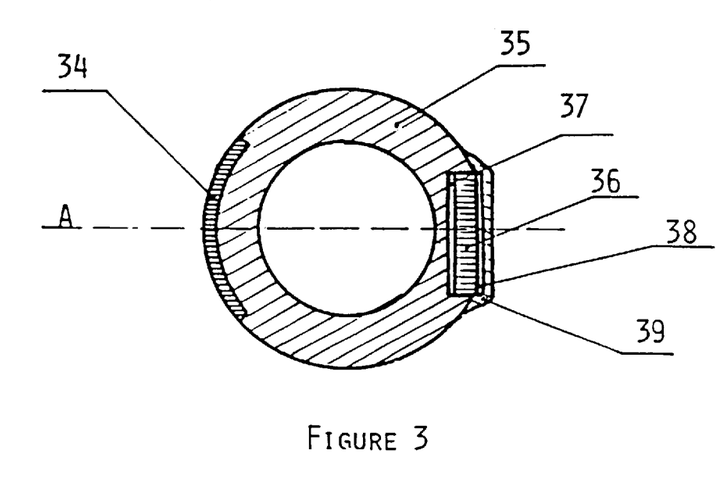
FIG. 3 is a radial plane cross-section of the same catheter at the site of the electrode and ultrasonic transducer.

Referring to FIG. 3, the radial cross-section of the catheter from FIG. 1 is disclosed without necessary electrical connections. The ablation electrode 34 is a metal plate embedded within the contours of the hollow plastic catheter body 35. An ultrasonic marking transducer 36 is mounted fixedly at the opposite side to the electrode 34. Transducer 36 is disclosed to be a piezoelectric platelet comprising metallized layers 37 and 38 which are the transducer electrodes. An ultrasonically matched layer 39 covers the transducer 36 for the purpose of electric insulation as well as mechanical and chemical isolation. Dashed line A designates the axial cross-section of the next figure.

Figure 4:
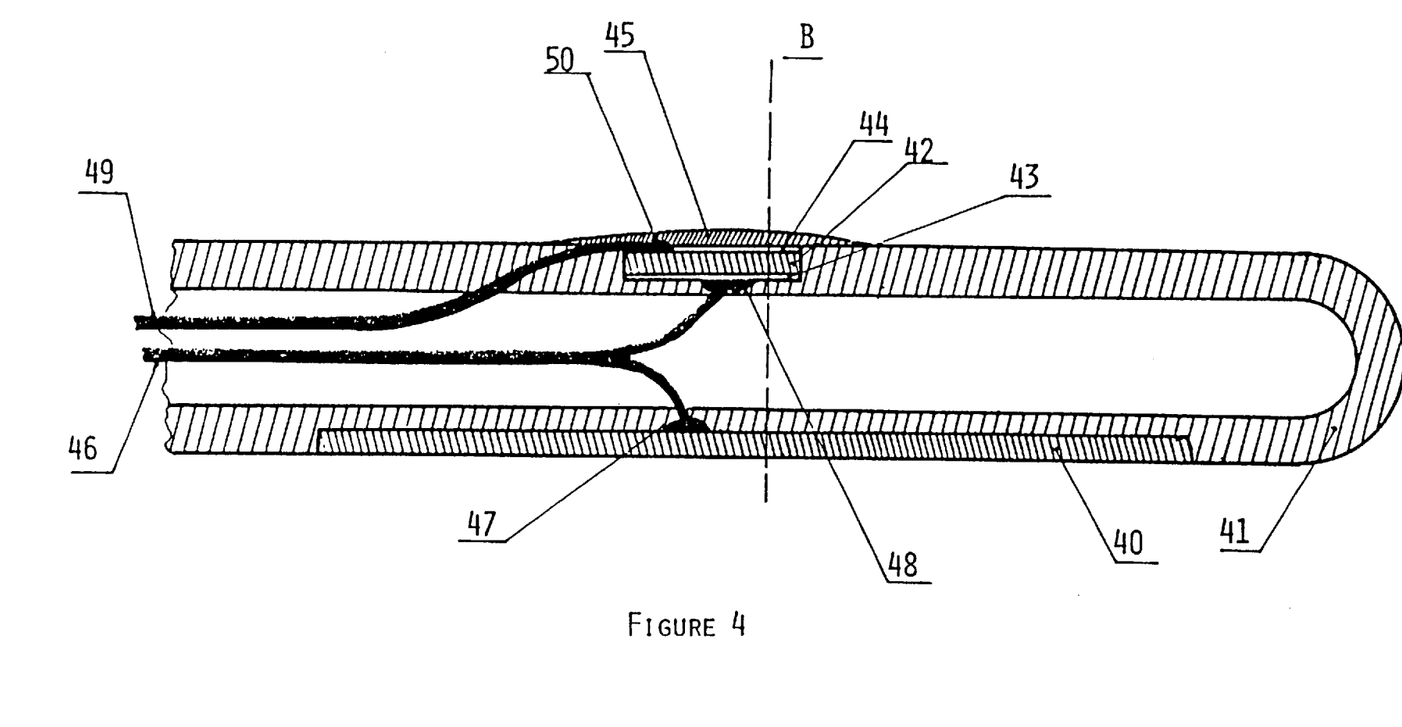
FIG. 4 is an axial cross-section of the same catheter at the same site.

Referring to FIG. 4, there is disclosed an axial cross-section of the distal part of a catheter from previous figures, as defined by dashed line A in FIG. 3. Dashed line B designates the radial cross-section disclosed in previous FIG. 3. The ablation electrode 40 is mounted fixedly embedded within the plastic hollow catheter body 41. Piezoelectric platelet 42 comprises metallized layers 43 and 44 being the ultrasonic transducer electrodes. Transducer 42 is mounted fixedly within the catheter body 41 and is covered by an ultrasonically matched insulation layer 45. Electric wire 46 is bifurcated at its distal end and soldered to the electrode 40 by means of the soldering joint 47 as well as to the transducer electrode 43 by means of the soldering joint 48. Electric wire 49 is soldered to the transducer electrode 44 by means of the soldering joint 50. In disclosed electric connection, the ultrasonic signal is led through wires 46 and 49, while the ablation energy is delivered through the wire 46. Instead of the soldering joints, the conductive gluing is also applicable. Disclosed ablation catheter assembly is the illustration of the one possible embodiment. There is no limitation to use the same principle in multiluminal catheter tubes. For the purpose of either radiofrequency or microwave energy ablation, the catheter wires will be specially designed to be coaxial in order to prevent the energy losses and dissipation within the catheter as well as to prevent the interference between ultrasonic circuit and ablation circuit.

Figure 5:
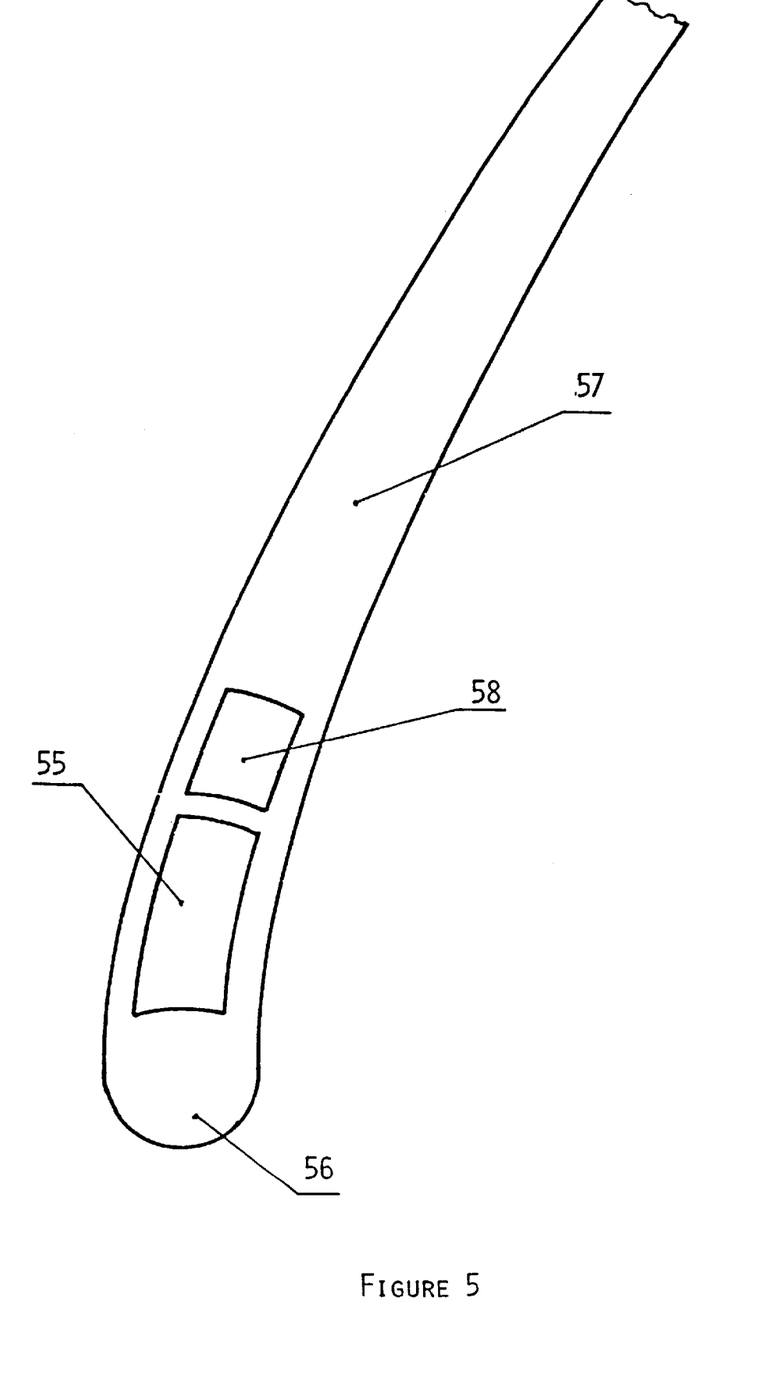
FIG. 5 is a perspective view of an ultrasonically marked ablation catheter providing identical direction of electric and ultrasonic fields.

Referring to FIG. 5, there is disclosed a distal portion of an ablation catheter capable to generate directional ultrasonic marking field as well as directional ablation field directed to the same direction. The catheter comprises a metal plate 55 being the ablation electrode, mounted fixed at the tip 56 of the catheter body 57. Adjacent to the electrode 55, there is a marking transducer assembly 58.

Figure 6:
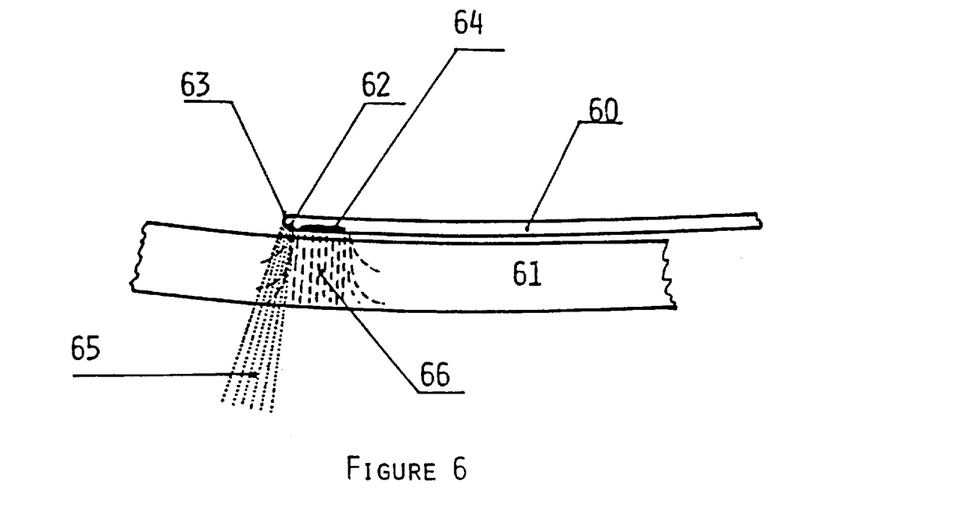
FIG. 6 is a schematic disclosure of application of the catheter from previous figure within the heart.

Referring to FIG. 6, there is disclosed a schematic illustration of the application of the catheter similar to that disclosed in FIG. 5. The catheter 60 is implanted at the cardiac muscle wall 61. For the purpose of illustration of another possible arrangement of that in FIG. 5, the marking transducer assembly 62 is mounted fixedly adjacent to the catheter tip 63. Ablation electrode 64 is mounted fixedly proximate to the marking transducer assembly 62. Unidirectional fields are generated: the ultrasonic one 65 for the purpose of marking as well as the electric one 66 for the purpose of tissue ablation within the myocardial wall 61.

Figure 7:
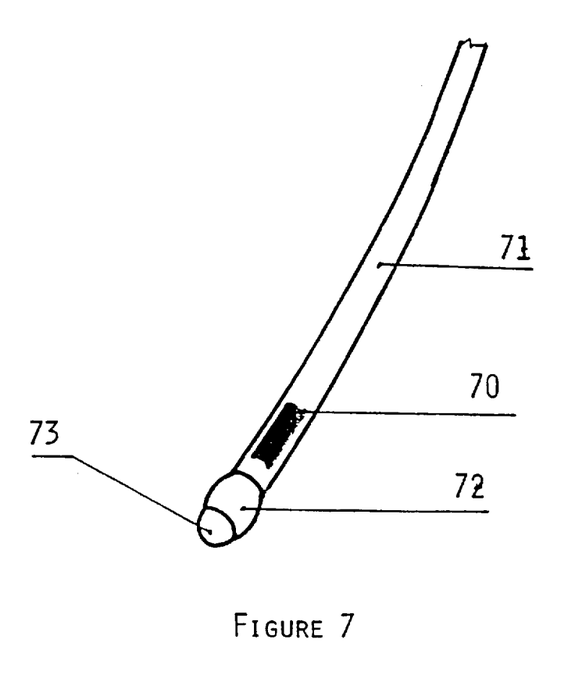
FIG. 7 is a perspective view of an ultrasonically marked ablation catheter providing omnidirectional ultrasonic and directional electric field.

Referring to FIG. 7, there is disclosed a distal portion of an ablation catheter capable to generate omnidirectional as well as directional fields for ultrasonic marking, and a directional electric field for ablation. An ablation electrode 70 being a metal plate is mounted fixedly embedded within the catheter plastic body 71. The marking transducer assembly 72 is mounted fixedly at the tip 73 of the catheter.

Figure 8:
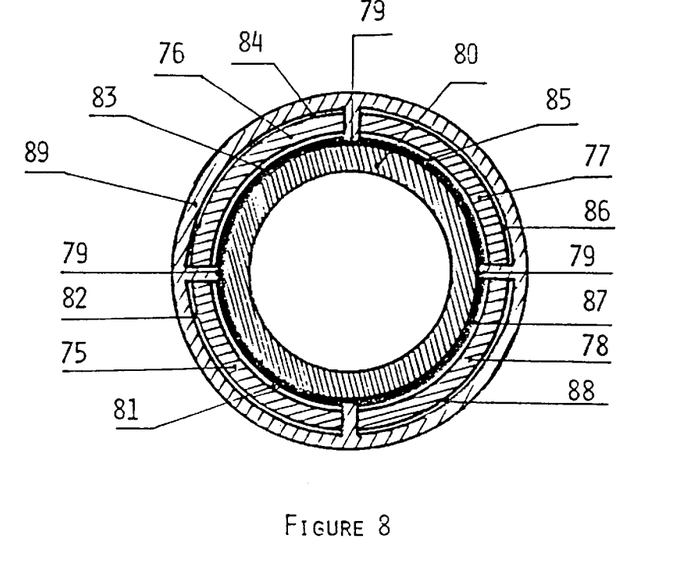
FIG. 8 is a cross-section of the catheter from previous figure at the site of the ultrasonic transducer.

Referring to FIG. 8, the radial cross-section of the marking transducer assembly is disclosed. Transducer assembly consists of the four piezoelectric segments 75, 76, 77 and 78 mounted fixedly by means of the soldering joint 79 to the reinforcement tube 80. Piezoelectric segments are disclosed to be cut from the tubiform piezoelectric transducer. In another possible embodiment (not shown), it also convenient to use the four piezoelectric platelets. Piezoelectric transducers comprise their electrodes which are the metallized layers: transducer 75 has electrodes 81 and 82, transducer 76 has electrodes 83 and 84, transducer 77 has electrodes 85 and 86, and transducer 78 has electrodes 87 and 88. The transducer segments are fixed to the metal reinforcement tube 80 actually with their electrodes 81, 83, 85 and 87, being soldered by means of the soldering joint 79. Therefore the reinforcement tube 80 is also the common electric connection for all four transducer segments. Transducer assembly is covered by means of an insulating ultrasonically matched thin layer 89.

Figure 9:
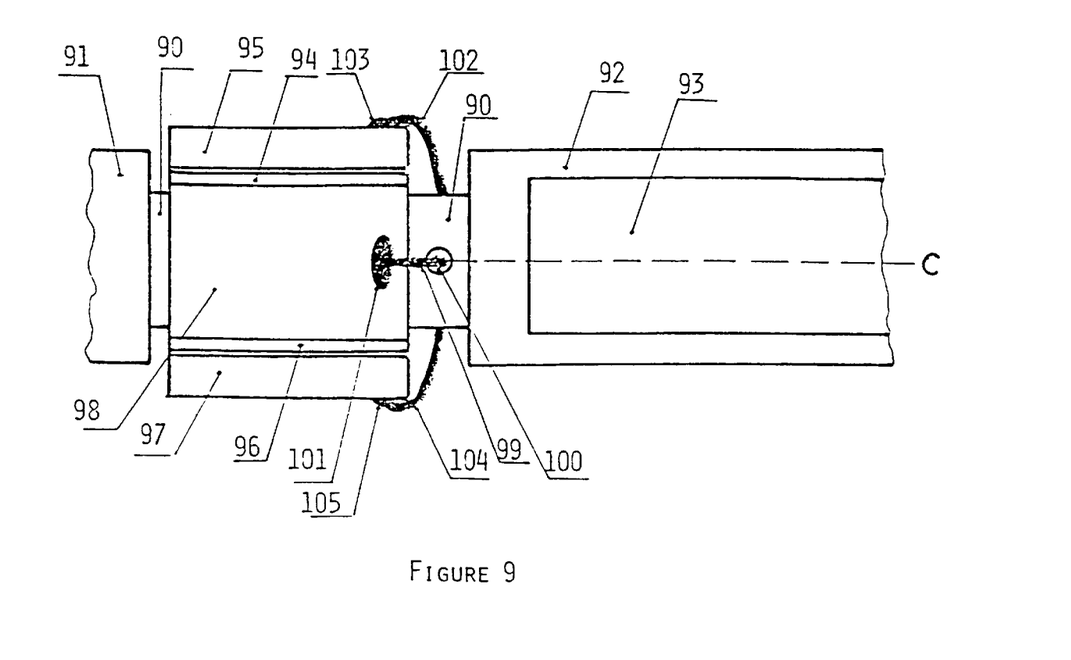
FIG. 9 is a view on the omnidirectional ultrasonic transducer assembly and ablation electrode surface.

Referring to FIG. 9, there is disclosed how the reinforcement tube 90 (designated by 80 in previous figure) mechanically connects the tip 91 of the catheter with the proximal part 92 of the catheter. The metal plate electrode 93 for ablation is mounted fixedly adjacent to the marking transducer assembly which is disclosed without the ultrasonically matched insulative layer to illustrate the details of the mounting rig. In this projection, only three transducer segments can be disclosed comprising piezoelectric segment 94 with its external transducer electrode 95, piezoelectric segment 96 with its external transducer electrode 97, as well as the transducer electrode 98 of the third piezoelectric segment which cannot be disclosed from this angle of view. Insulated wire 99 is conducted through the hole 100 (drilled on the reinforcement tube 90), and soldered to the transducer electrode 98 by means of the soldering joint 101. Another wire 102, emanating through the reinforcement tube 90, is soldered to the transducer electrode 95 by means of the soldering joint 103. The third wire 104, emanating through the reinforcement tube 90, is soldered to the transducer electrode 97 by means of the soldering joint 105. The dashed line of cross-section for the next figure is designated by C.

Figure 10:
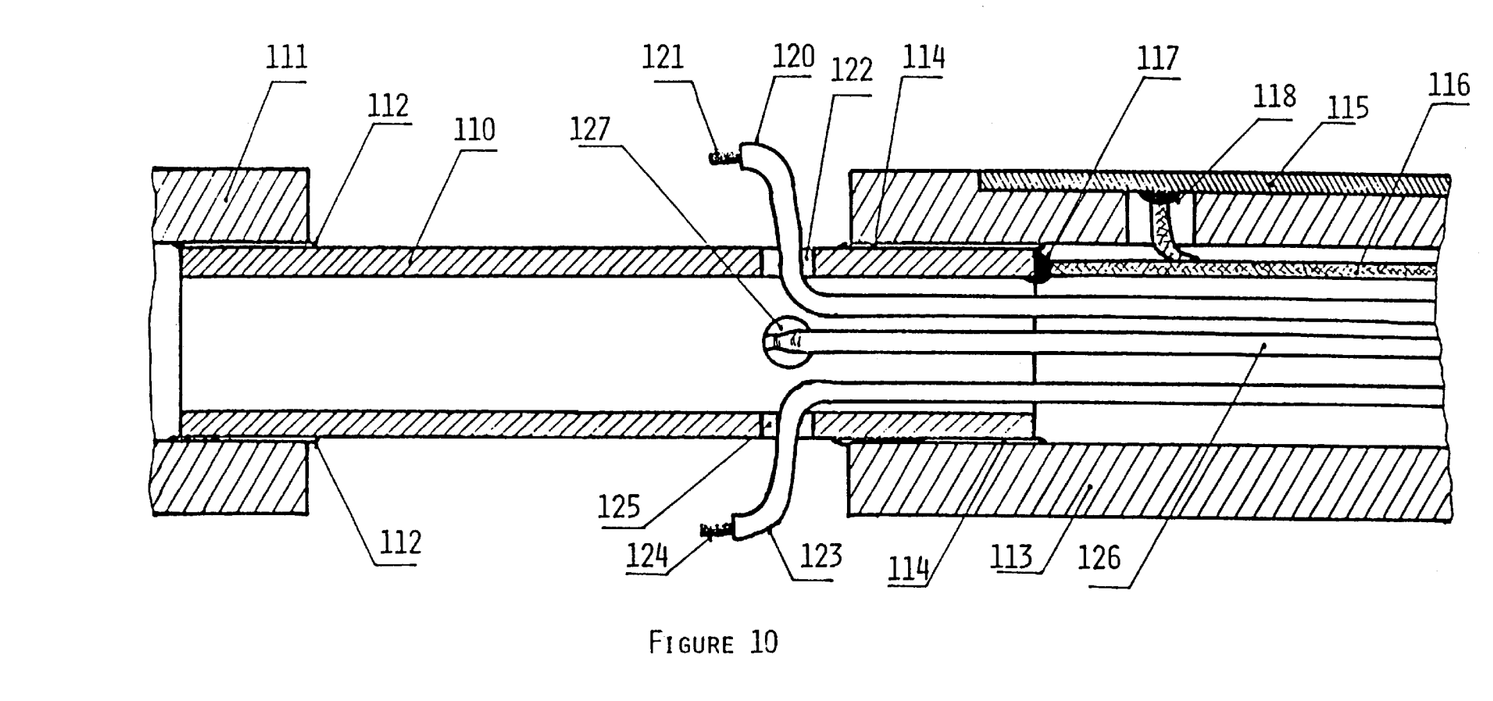
FIG. 10 is an axial cross-section of the catheter at the site of the ultrasonic transducer attachment.

Referring to FIG. 10, there is disclosed the axial cross-section through the reinforcement tube 110 (designated with 90 in FIG. 9 and with 80 in FIG. 8). The marking transducer segments are not mounted in order to illustrate the preparation of electric connections and conduction of wires through the reinforcement tube. The distal part 111 of the catheter body, which is actually close to the catheter tip, is mechanically fixed to the reinforcement tube 110 by means of the adhesive layer 112. The proximal part 113 of the catheter body is mechanically fixed to the reinforcement tube 110 by means of the adhesive layer 114. The ablation electrode 115 is mounted fixedly on the hollow plastic body 113. An uninsulated wire 116, bifurcated at its distal end is electrically connected to the reinforcing tube 110 by means of the soldering joint 117, as well as to the electrode 115 by means of the soldering joint 118. Insulated wire 120 is prepared for the soldering with its uninsulated end 121 to the external transducer electrode of one piezoelectric segment (not shown), and is conducted through the hole 122 in the reinforcement tube 110. Insulated wire 123 is prepared for the soldering with its uninsulated end 124 to the external transducer electrode of one piezoelectric segment (not shown), and is conducted through the hole 125 in the reinforcement tube 110. Insulated wire 126 is prepared for the soldering with its uninsulated end (not shown) to the external transducer electrode of one piezoelectric segment (not shown), and is conducted through the hole 127 in the reinforcement tube 110. The fifth wire is not shown in this projection.

In disclosed embodiment of FIGS. 7, 8, 9 and 10, the marking transducer segments may be separately connected to the ultrasonic marking circuits by means of the common wire 116 and special four wires connected to the external transducer electrodes. If all four segments are connected to the marking circuits simultaneously, the omnidirectional ultrasonic field assures the proper marker for the purpose of implantation guidance. If one of the segments is connected to the marking circuits, directional ultrasonic field enables the marker for the purpose of determination of the radial orientation of the electrode. Moreover, switching different single segment enables four different marker radial positions: at the ablation electrode, opposite to the ablation electrode, and two positions at 90 degrees to the ablation electrode. For example, if the wire 99 and reinforcement tube 90 (disclosed in FIG. 9) are connected to the ultrasonic marking circuit, the marker occurs when the ablation electrode 93 is orientated towards the scanner probe. It is understood that other modes of electrical connections are possible, specially in multiluminal catheter bodies and by means of the coaxial cables. However, the principle remains always the same as disclosed herein.

Figure 11:
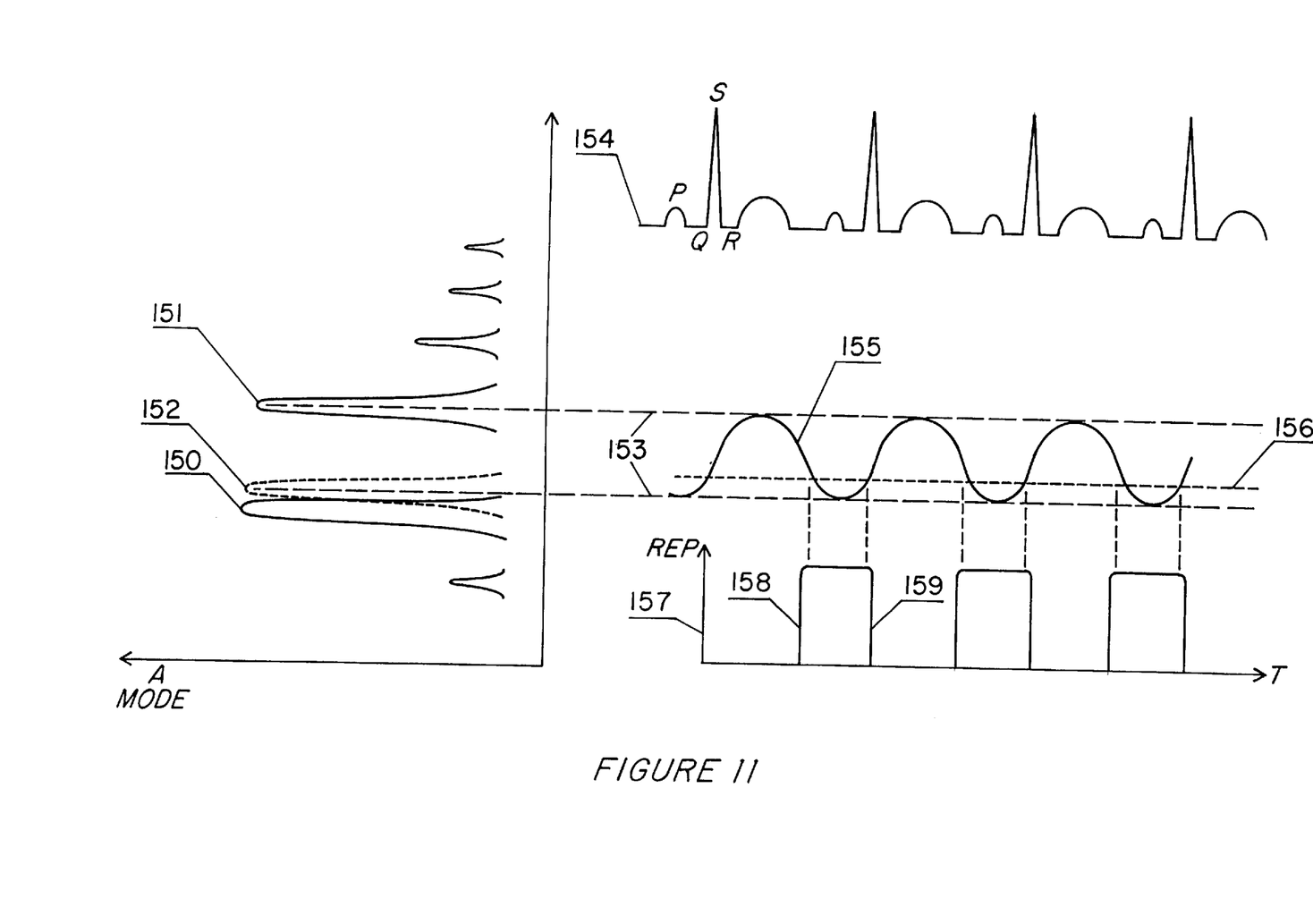
FIG. 11 shows the waveforms of the A-mode ultrasonic signal, the ECG and the ablation power, disclosing the principle of the proximity monitoring and power modulation.

Referring to FIG. 11, there is disclosed the principle of the proximity modulation of the radiofrequency ablation power. The ultrasonic field 65 produced by transducer 63, as designated in FIG. 6, may be used for monitoring of the distance between transducer 63 and myocardial wall 61. This distance actually represents also the distance between ablation electrode 64 and myocardial wall 61.

It is known in the art that the electric field strength decreases with the square of the distance. Therefore every ablation electrode dislodgement i.e. increase of the distance between ablation electrode and cardiac tissue, causes significant losses of ablation energy, as well as dissipation in the surrounding blood and tissue which may cause blood coagulation and thromboembolic incident.

Directional marking transducer may be connected to the echocardiographic scanner for instance with passive system for marking purpose in 2D image and ultrasonically guided implantation of the catheter. Within the A-mode echographic circuits, the signal may be obtained as disclosed on diagram of FIG. 11. First echo signal peak 150 is the echo from the myocardial wall wherein exists the tissue intended for ablation. Second echo signal peak 151 is the signal of the marker transducer. This second signal peak is rhythmically shifted in the left-right manner, as the cardiac contraction provokes the catheter tip movement and consequent microdislodgement. The signal peak 151 is disclosed in the moment of maximal distance of the marker transducer from the myocardium. Dashed contour 152 represents the position of the echo signal peak 151 in the moment when the marking transducer remains in the intimate contact with the myocardium. Dashed lines 153 represent the magnitude of the electrode dislodgement. Catheter dislodgement is rhythmic i.e. the movements of the catheter within the heart are synchronous with certain mechanical event within the cardiac cycle. Catheter may move either during the cardiac contraction, or during the cardiac relaxation. The mode of catheter movement is a consequence of unforeseen events, but it is usually synchronous with ECG signal. Therefore the waveform of the proximity 155 as a function of time of the marking transducer relatively to the myocardial wall is shown in timing correlation with ECG waveform 154. Dotted line 156 depicts the trigger level for the proximity switch of the radiofrequency ablation energy source. The waveform 157 of the radiofrequency power (designated by "RFP") as a function of time (designated by "T") is disclosed in exact timing correlation with the proximity waveform 155. Whenever the proximity value between the marking transducer and the myocardial wall falls bellow the trigger level determined by line 156, the radiofrequency power is switched-on (158). Whenever the proximity value between the marking transducer and the myocardial wall raises above the trigger level determined by line 156, the radiofrequency power is switched-off (159). In this mode of operation. the radiofrequency energy source generates a periodic waveform of the power which is synchronous with the cardiac mechanical events.

If a DC shock is used for ablation procedure, the same principle may be used for firing the defibrillator pulse synchronously with the QRS complex but in connection with the proximity switch i.e. during the period when the proximity value is small. Actually this means that the QRS detector signal (having logical "1" during the QRS duration) and proximity detector (having logical "1" when function 155 is bellow trigger level 156) signal must be processed by means of the Boolean AND gate in order to get the logical "1" to fire the defibrillator pulse.

While specific embodiments of present invention have been described, it should be understood that these embodiments are described for purposes of illustration only. The foregoing description is not intended in any way to limit the scope of the present invention. Rather is the intention that the scope of the invention be limited only as defined in the appended claims.

Figure 12:
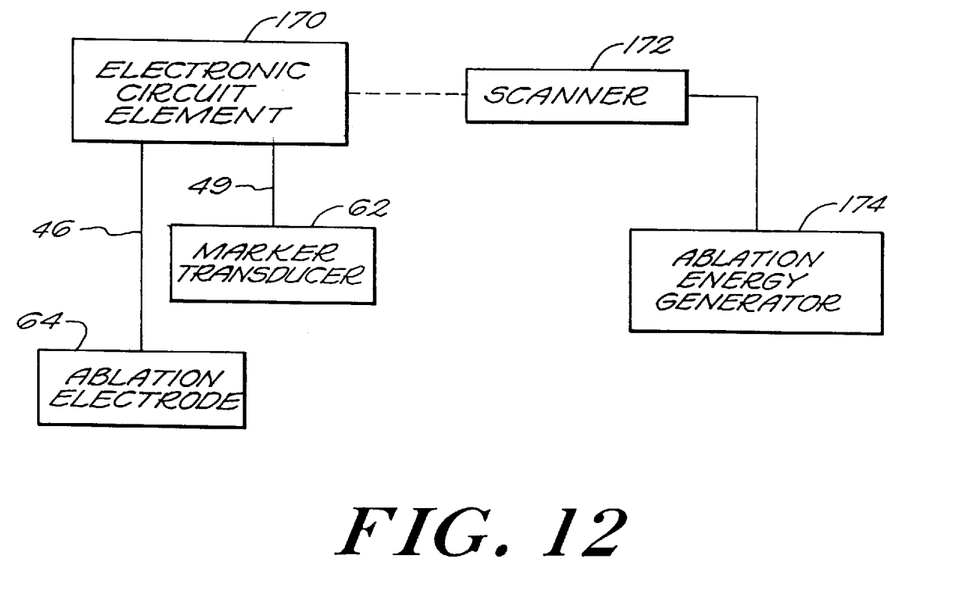
FIG. 12 is a functional block diagram illustrating an electronic circuit element for use with the ablation electrode and the marker transducer of the catheter, for modulating the ablation energy supplied to the ablation electrode in response to the proximity of the electrode to tissue.

With reference to FIG. 12, the invention can include an electronic circuit element 170, connectable or connected to the ablation electrode, 64 and to the transducer assembly 62, for transmitting signals into and receiving signals from the transducer assembly 62 and the ablation electrode 64.

The electronic circuit element 170 uses signals from the transducer 62 for ranging and position assessment relative to outside and internal bodily structures. The electronic circuit element 170 can facilitate the steering and measurement of the ablation procedure, in particular the steering of the moment of release of the ablation energy, and can include an outside ultrasonic scanner 172 capable of localizing an area in an ultrasonic cardiographic image only within which the release of the ablation energy is required. The ultrasonic scanner 172 can be connected to an ablation energy generator 174.

The piezoelectric transducer assembly 62 and the ablation electrode 64 can be connected to the electronic circuit element 170 via the lengthwise conductors 46 and 49, and can be capable of detecting incoming electrical signals received from the piezoelectric transducer 62 and representing ultrasonic pulses. The electronic circuit element 170 can also be adapted for transmitting electrical signals to the transducer assembly 62 for producing ultrasonic pulses. The electronic circuit element 170 can be adapted for using the transmitted and received signals to localize, via A mode ranging, the position of the ablation electrode 64, and can also be adapted for using the transmitted and received signals for localization of the position of the ablation electrode 64 using a M-mode distance measurement. Additionally, the electronic circuit element 170 can be adapted for using the transmitted and received electrical signals for localization of the position of the ablation electrode 64 by means of introduction into a B-mode two dimensional image, or by means of a Doppler velocity measurement.

The electronic circuit element 170 can also use the transmitted and received electrical signals for localization of the position of the ablation electrode 64 by means of detection of coincidence of a predetermined position in either A, B, or M-mode or velocity as measured by the electronic circuit element 170 in conjunction with an outside scanner 172. An operator's request for delivery of the ablation energy is satisfied only in the case of such a coincidence.

The electronic circuit element 170 can be capable of generating electrical signals for producing ultrasound pulses and to detect echoes e.g., 150, 151, 152, from heart structures by transmitting and receiving of electrical signals representing ultrasonic pulses, and can also be capable of measuring the distance 153 between, for example, the transducer 62 and the heart tissue 61.

The electronic circuit element 170 can be adapted for detecting the QRS complex of the electrocardiogram 154, and can be capable of generation a proximity function 155 for characterizing the variation of the distance 153 in time. The electronic circuit element 170 can also be adapted for identifying the crossing of the proximity function 155 over the preset and adjustable levels 156 within the measured distance 153. The electronic circuit element 170 can be adapted for modulating the power 157 of the ablation signal in such as way such that the power appears only in a time interval between the time points 158, 159 wherein the proximity function 155 crosses the predetermined trigger level 156. Accordingly, the power of the ablation signal is delivered to the ablation electrode 64 only when the transducer assembly 62 is in proximity to the heart tissue.

We claim:
1. A cardiac ablation device comprising
an axially elongated catheter body (10, 28, 31, 35, 41, 57, 60, 71) for implantation in the human heart and having an ablation electrode (12, 34, 40, 55, 64, 70) adapted for contacting the heart;
said catheter body including an ultrasonic transducer assembly (13, 36, 42, 58, 62, 72) at a location adjacent to said ablation electrode;
said catheter body including two electrical conductors (46, 49), which are provided with terminals at the proximal end of the catheter, and which are adapted for transmitting a high frequency electrical signal to and from said transducer assembly (42) and for transmitting an ablation signal to said electrode (40);

said transducer assembly (13, 36, 42, 58, 62, 72) being adapted to produce, in a direction radial to said axially elongated body at the location of the transducer assembly, a directional acoustic ultrasonic field (29, 32, 65) when supplied with said high frequency electrical signal and said ablation electrode (12, 34, 40, 55, 64, 70) being adapted to produce in a direction radial to said axially elongated catheter body at the location of the transducer assembly, a directional electric ablation field (30, 33, 66) when supplied with said ablation signal; and said transducer assembly and said ablation electrode being arranged in a predetermined mutual positional relationship so that the radial direction in which said electric ablation field is produced is exactly determined relative to the radial direction in which said acoustic ultrasonic field is produced.

2. Device according to claim 1, wherein direction of said electric ablation field (30) can be determined within the structures of the heart whenever direction of said acoustic field (29) within the structures of the heart is determined by means of processing of said electrical signal from said ultrasonic field, said processing providing the marker within an echocardiographic image pointing the direction of said acoustic field towards the echocardiographic scanner probe (27).

3. Device according to claim 1, wherein said ablation electrode (12, 34, 40, 55, 64, 70) is a plate of a maximum width of one quarter of the circumference of said catheter body.

4. Device according to claim 1, wherein said transducer assembly (13, 36, 42, 58, 62) comprises a platelet of a width of approximately one quarter of the circumference of said catheter body, and which is made of piezoelectric material having two metallized layers (37/38, 43/44) being the transducer electrodes polarizing said transducer in radial direction relatively to said catheter body.

5. Device according to any of claim 4, wherein said transducer assembly is a platelet having width and length such as to generate a directive characteristic (29, 32, 65) at its operation frequencies, the directivity of the main lobe not exceeding 60 degrees.

6. Device according to claim 4, wherein said piezoelectric platelet (36, 42) is covered on the outer side by an insulating and isolating layer (39, 45).

7. Device according to claim 1, having said electrode and said transducer assembly positioned near the tip of said catheter body (11, 56, 63, 73).

8. Device according to claim 1, wherein the mutual distance between the said ablation electrode and the said ultrasonic transducer assembly is less than half of the length of said transducer assembly.

9. Device according to claim 1, wherein the axis of the directivity of said electric ablation field (66) and the axis of the directivity of said acoustic ultrasonic field (65) coincide.

10. Device according to claim 1, wherein the axis of the directivity of said electric ablation field (30, 33) and the axis of the directivity of said acoustic ultrasonic field (29, 32) are at any fixed azimuthal angle including 180 degrees.

11. Device according to claim 1, wherein said electrode and said transducer assembly do not protrude unessentially from the outside profile of said catheter body.

12. Device according to claim 1, wherein said transducer assembly comprises a cylindrical array of piezoelectric transducers (75, 76, 77, 78) facing in all azimuthal directions.

13. Device according to claim 12, wherein each of said piezoelectric transducers (75, 76, 77, 78) comprises two metallized layers (81/82, 83/84, 85/86, 87/88) being the transducer electrodes polarizing said transducers in radial direction relatively to said catheter body.

14. Device according to claim 12, wherein said transducers (75, 76, 77, 78) are fixed onto a reinforcement tubelet or rig (80, 90) by means of the conductive adhesive joint (79) which electrically connects the inner array of said transducer electrodes (81, 83, 85, 87) with said reinforcement (80, 90).

15. A cardiac ablation device comprising
an axially elongated catheter body (10, 28, 31, 35, 41, 57, 60, 71) for implantation in the human heart and having an ablation electrode (12, 34, 40, 55, 64, 70) adapted for contacting the heart;

said catheter body including an ultrasonic transducer assembly (13, 36, 42, 58, 62, 72) at a location adjacent to said ablation electrode;

said catheter body including two electrical conductors (46, 49), which are provided with terminals at the proximal end of the catheter and which are adapted for transmitting a high frequency electrical signal to and from said transducer assembly (42) and for transmitting an ablation signal to said electrode (40);

said transducer assembly (13, 36, 42, 58, 62, 72) being adapted to produce a directional acoustic ultrasonic field (29, 32, 65) when supplied with said high frequency electrical signal and said ablation electrode (12, 34, 40, 55, 64, 70) being adapted to produce a directional electric ablation field (30, 33, 66) when supplied with said ablation signal;

said transducer assembly and said ablation electrode being arranged in a predetermined mutual positional relationship so that the direction of said electric ablation field is determined relative to the direction of said acoustic ultrasonic field;

wherein said transducer assembly comprises a cylindrical array of piezoelectric transducers (75, 76, 77, 78) facing in all azimuthal directions;

wherein said transducers (75, 76, 77, 78) are fixed onto a reinforcement tubelet or rig (80, 90) by means of the conductive adhesive joint (79) which electrically connects the inner array of said transducer electrodes (81, 83, 85, 87) with said reinforcement (80, 90); and wherein said transducers of said array are connected to the proximal end of said catheter body via lengthwise conductors (99, 102, 104) running along and inside of the said catheter body and being connected to outer array of said transducer electrodes (98, 95, 97) by means of joints (101, 103, 105), said conductors being adapted to transmit high frequency ultrasonic signals to and from said transducer array, in such a way as that the signal of each single transducer of said transducer array is provided between said reinforcement and each single of said lengthwise conductors respectively.

16. Device according to claim 1 further comprising
an electronic circuit means connectable or connected to said ablation electrode and to said transducer assembly, capable of transmitting signals into and receiving signals from said transducer assembly and said ablation electrode, in order to utilize said signals from said transducer for ranging and position assessment relative to outside and internal bodily structures.

17. Device according to claim 16, wherein said electronic circuit means are utilized for ablation procedure steering and measurement, in particular steering of the moment of the release of the ablation energy.

18. Device according to claim 16, wherein said electronic circuit means within an outside ultrasonic scanner connected to ablation energy generator are capable to localise an area in the ultrasonic echographic image only within which the release of ablation energy is required.

19. Device according to claim 16, wherein said piezoelectric transducer assembly is connected to said electronic circuit means via the said lengthwise conductors whereby said electronic circuit means being capable of detecting incoming electrical signals received from said piezoelectric transducer assembly and representing ultrasonic pulses.

20. Device according to claim 16, wherein said piezoelectric transducer assembly connected to said electronic circuit means via said lengthwise conductors whereby said electronic circuit means being capable of transmitting electrical signals to said transducer assembly for producing ultrasonic pulses.

21. Device according to claim 16, wherein said piezoelectric transducer assembly is connected to said electronic circuit means via the said lengthwise conductors whereby said electronic circuit means being capable of detecting incoming electrical signals received from said piezoelectric transducer assembly and representing ultrasonic pulses and whereby said electric circuit means being capable of transmitting electrical signals to said transducer assembly for producing ultrasonic pulses.

22. Device according to claim 21, wherein said electronic circuit means being capable of utilising said transmitted and received electrical signals for localisation of the position of said ablation electrode by means of A mode ranging.

23. Device according to claim 22, wherein said electronic circuit means being capable of utilising said transmitted and received electrical signals for localisation of the position of said ablation electrode by means of being capable of detection of coincidence of a predetermined position in either A, B, or M mode or velocity as measured in conjunction with outside ultrasonic scanner with the operators request for delivery of the ablation energy being satisfied only in case of such a coincidence.

24. Device according to claim 23, wherein said electronic circuit means being capable to generate electrical signals for producing ultrasound pulses and to detect echoes (150, 151, 152) from heart structures by means of transmission and reception of electrical signals representing ultrasonic pulses.

25. Device according to claim 23, wherein said electronic circuit means being capable to measure the distance (153) between said transducer (62) and the heart tissue (61).

26. Device according to claim 25, wherein said electronic circuit means being capable to generate a proximity function (155), characterising the variation of said distance (153) in time.

27. Device according to claim 23, wherein said electronic circuit means being capable to detect the QRS complex of the electrocardiogram (154).

28. Device according to claim 21, wherein said electronic circuit means being capable of utilising said transmitted and received electrical signals for localisation of the position of said ablation electrode by means of M mode distance measurement.

29. Device according to claim 21, wherein said electronic circuit means being capable of utilising said transmitted and received electrical signals for localisation of the position of said ablation electrode by means of introduction into B mode two dimensional image.

30. Device according to claim 21, wherein said electronic circuit means being capable of utilising said transmitted and received electrical signals for localisation of the position of said ablation electrode by means of Doppler velocity measurement.

31. A cardiac ablation device comprising
   an axially elongated catheter body (10, 28, 31, 35, 41, 57, 60, 71) for implantation in the human heart, having an ablation electrode (12, 34, 40, 55, 64, 70) adapted for contacting the heart;
   said catheter body including an ultrasonic transducer assembly (13, 36, 42, 58, 62, 72) at a location adjacent to said ablation electrode;
   said catheter body including two conductors (46, 49), which are provided with terminals at the proximal end of the catheter, and are adapted for transmitting a high frequency electrical signal to and from said transducer assembly (42) and for transmitting an ablation signal to said electrode (40);
   said transducer assembly (13, 36, 42, 58, 62, 72) being adapted to produce a directional acoustic ultrasonic field (29, 32, 65) when supplied with said high frequency electrical signal and said ablation electrode (12, 34, 40, 55, 64, 70) being adapted to produce a directional electric ablation field (30, 33, 66) when supplied with said ablation signal;
   said transducer assembly and said ablation electrode being arranged in a predetermined mutual positional relationship so that the direction of said electric ablation field is determined relative to the direction of said acoustic ultrasonic field;
   wherein said transducer assembly comprises a cylindrical array of piezoelectric transducers (75, 76, 77, 78) facing in all azimuthal directions;
   an electronic circuit means for connection to said ablation electrode and to said transducer assembly and for transmitting signals to and receiving signals from said transducer assembly and said ablation electrode, and for using said signals from said transducer for ranging and position assessment relative to outside and internal bodily structures;
   said piezoelectric transducer assembly being connected to said electronic circuit means via lengthwise conductors whereby said electronic circuit means detects incoming electrical signals received from said piezoelectric transducer assembly representing ultrasonic pulses and whereby said electronic circuit means is capable of transmitting electrical signals to said transducer assembly for producing ultrasonic pulses;
   said electronic circuit means being capable of utilizing said transmitted and received electrical signals for localization of the position of said ablation electrode by means of A mode ranging;
   said electronic circuit means being further capable of utilizing said transmitted and received electrical signals for localization of the position of said ablation electrode by detection of coincidence of a predetermined position in either A, B, or M mode or velocity as measured in conjunction with an outside ultrasonic scanner, an operators request for delivery of the ablation energy being satisfied only in case of such a coincidence;
   said electronic circuit means is capable of measuring the distance (153) between the said transducer (62) and the heart tissue (61), and of generating a proximity function (155), characterizing the variation of said distance (153) in time; and
   wherein said electronic circuit means is capable of identifying crossing of said proximity function (155) over a preset and adjustable levels (156) within the measured distance (153).

32. Device according to claim 31, wherein said electronic circuit means being capable to modulate the power (157) of said ablation signal in such a way as to said power to appear only within a time interval between the time points (158, 159) wherein said proximity function (155) crosses the predetermined trigger level (156).

33. Device according to claim 30, wherein said power of said ablation signal is delivered to said ablation electrode only when said transducer assembly is in proximity to said heart tissue.

34. A cardiac ablation catheter apparatus comprising
a catheter body having an elongation axis and adapted for implantation in a human heart,
ablation means, mounted with said catheter body, for receiving ablation energy from an ablation energy source and for generating an ablation field for ablating tissue,
said catheter body further mounting a transducer operable for generating an ultrasonic field for monitoring the proximity of said ablation electrode to tissue,
electronic circuit means, electrically connected to said transducer and to said ablation means, for monitoring the proximity of said ablation means to tissue and for modulating the ablation of tissue by said ablation means within the cardiac cycle in response to a selected proximity of said ablative means to tissue.

35. The apparatus of claim 34 wherein said electronic circuit means includes means for continuously monitoring the proximity of said ablation electrode to tissue.

36. The apparatus of claim 34 wherein said ablation means includes an electrode and wherein said ablation field includes an electric field generated by said electrode.

37. The cardiac ablation catheter apparatus of claim 36 wherein said ablation electrode generates a directional ablation electric field in first known direction relative to the catheter body, and wherein said transducer generates an ultrasonic field along a second known direction relative to the catheter body and having a known direction relative to the first direction of the ablation field.

38. The cardiac ablation catheter apparatus of claim 37 wherein said transducer generates a directional ultrasonic field, and wherein said first and second known directions are radial to said catheter body.

39. The cardiac ablation catheter apparatus of claim 36 wherein said electronic circuit means modulates the ablation energy received by said ablation electrode such that the ablation electrode ablates tissue only when said ablation electrode is within a selected distance of the tissue.

40. A cardiac ablation catheter apparatus comprising
a catheter body having an elongation axis and adapted for implantation in a human heart and adapted for twisting about the elongation axis,
said catheter body mounting an ablation means for receiving ablation energy for generating, in a known first direction, a directional tissue ablating field, said first direction being radial to the elongation axis of the catheter body, and
said catheter body further mounting a marker transducer operable for generating a directional ultrasonic field along a second known direction radial to the catheter body, said second direction being known relative to said first direction, such that said ablation field generated by said ablation means can be directed to a preferred volume of tissue by imaging said marker transducer and radially twisting the catheter body.

41. The apparatus of claim 40 wherein said ablation means includes an ablation electrode and wherein said ablation field includes an electric field generated by said ablation electrode.

42. A method for directing an ablation field toward a preferred cardiac tissue volume, comprising the steps of
providing a catheter body elongated along an elongation axis and adapted for implantation in a heart and adapted for twisting about the elongation axis,
mounting with the catheter body an ablation electrode for receiving ablation energy for generating, in a known first direction radial to the elongation axis of the catheter body, a directional ablation field,
mounting with the catheter body a marker transducer for producing, along a known second direction radial to the catheter body, a directional marker field, the known second direction being known relative to the known first direction,
implanting the catheter body and the ablation electrode and marker transducer
mounted therewith into the heart
imaging the marker field, and
positioning the ablation electrode such that the ablation field generated thereby is directed toward the preferred tissue volume by radially twisting the catheter in response the image of the marker field and the known first and second directions and the relationship therebetween.

43. A method for ablating cardiac tissue, comprising the steps of
providing a catheter body elongated along an elongation axis and adapted for implantation in a heart,
mounting with the catheter body an ablation electrode for placement proximate to tissue, the ablation electrode for adapted for receiving ablation energy for generation of an ablation field,
mounting with the catheter body a marker transducer for producing a marker field for monitoring the proximity of said ablation electrode to cardiac tissue,
implanting the catheter body, including the ablation electrode and marker transducer mounted therewith, into the heart,
supplying ablative energy to the ablation electrode for ablating tissue,
monitoring the proximity of the ablation electrode to the tissue to be ablated, and
modulating the ablation of tissue by the ablative electrode with the cardiac cycle in response to a preselected proximity of the ablative electrode to the tissue.

44. The method according to claim 43 wherein the step of implanting the catheter body includes the step of imaging the marker field generated by the marker transducer to facilitate directing the ablative field towards the tissue to be ablated.

45. The method according to claim 44 wherein the ablation electrode is adapted for generating, in a known first direction, a directional tissue-ablating electric field, said first direction being radial to the elongation axis of the catheter body, and wherein the marker transducer is adapted for generating, along a second known direction radial to the catheter body, a directional ultrasonic field, said second direction being known relative to said first direction, and wherein the step of positioning the ablative electrode adjacent includes radially twisting the catheter body, in response the image of the marker field and the known first and second directions, including the relationship therebetween, to place the ablation electrode adjacent tissue to be ablated.

46. The method according to claim 43 wherein the step of modulating includes the step of generating an ablation field only when the ablation electrode is within a selected distance of the tissue to be ablated.

* * * * *

UNITED STATES PATENT AND TRADEMARK OFFICE
CERTIFICATE OF CORRECTION

PATENT NO. : 5,840,030
DATED : November 24, 1998
INVENTOR(S) : Ferek-Petric et al.

It is certified that error appears in the above-identified patent and that said Letters Patent is hereby corrected as shown below:

At column 7, lines 45-51, move the entire paragraph to the end of the specification and before the claims, i.e. to column 8, between lines 51 and 52.
At column 9, line 36, after "Device according to", delete "any of".
At column 14, line 40, change "with" to -- within --.

Signed and Sealed this

Twenty-first Day of December, 1999

Q. TODD DICKINSON

Attest:

Attesting Officer

Acting Commissioner of Patents and Trademarks